(12) United States Patent
Lattner et al.

(10) Patent No.: US 9,321,704 B2
(45) Date of Patent: Apr. 26, 2016

(54) CYCLOHEXANE DEHYDROGENATION

(71) Applicant: ExxonMobil Chemical Patents Inc., Baytown, TX (US)

(72) Inventors: James R. Lattner, LaPorte, TX (US); Christopher L. Becker, Manhattan, KS (US); Tan-Jen Chen, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/438,638

(22) PCT Filed: Dec. 2, 2013

(86) PCT No.: PCT/US2013/072539
§ 371 (c)(1),
(2) Date: Apr. 27, 2015

(87) PCT Pub. No.: WO2014/088922
PCT Pub. Date: Jun. 12, 2014

(65) Prior Publication Data
US 2015/0284304 A1    Oct. 8, 2015

Related U.S. Application Data

(60) Provisional application No. 61/733,732, filed on Dec. 5, 2012.

(30) Foreign Application Priority Data

Feb. 8, 2013    (EP) .................................... 13154528

(51) Int. Cl.
| | |
|---|---|
| C07C 45/00 | (2006.01) |
| C07C 37/80 | (2006.01) |
| C07C 2/74 | (2006.01) |
| C07C 5/367 | (2006.01) |
| C07C 5/31 | (2006.01) |
| C07C 13/28 | (2006.01) |
| C07C 15/04 | (2006.01) |
| C07C 37/58 | (2006.01) |
| C07C 45/28 | (2006.01) |

(52) U.S. Cl.
CPC . *C07C 5/367* (2013.01); *C07C 2/74* (2013.01); *C07C 5/31* (2013.01); *C07C 13/28* (2013.01); *C07C 15/04* (2013.01); *C07C 37/58* (2013.01); *C07C 45/28* (2013.01); *C07C 2101/14* (2013.01)

(58) Field of Classification Search
CPC .......... C07C 45/294; C07C 37/60; C07C 2/74
USPC .................... 568/342, 798; 585/252, 434, 467
See application file for complete search history.

(56) References Cited

U.S. PATENT DOCUMENTS

| | | | |
|---|---|---|---|
| 6,037,513 A | 3/2000 | Chang et al. | |
| 7,579,511 B1 | 8/2009 | Dakka et al. | |
| 2012/0271078 A1* | 10/2012 | Chen | C07C 2/74 585/252 |

FOREIGN PATENT DOCUMENTS

| | | |
|---|---|---|
| WO | WO 2009/131769 | 10/2009 |
| WO | WO 2010/042142 | 4/2010 |
| WO | WO 2011/096991 | 8/2011 |
| WO | WO2011/096998 A1 * | 8/2011 |
| WO | WO 2012/082409 | 6/2012 |

* cited by examiner

*Primary Examiner* — Sikarl Witherspoon
(74) *Attorney, Agent, or Firm* — Siwen Chen; Stephen A. Baehl (57) ABSTRACT

A cyclohexane dehydrogenation process comprising a step of providing, as a benzene-containing stream, a vapor phase in equilibrium with a liquid phase at a condensation separation system; supplying benzene, hydrogen, and cyclohexane into a dehydrogenation reactor where at least part of the benzene supplied is from the benzene-containing stream. The use of a condensation separation system enables the control of the partial pressure of benzene in the material fed into the dehydrogenation reactor by controlling the temperature of the vapor phase, and hence the control of hydrogen to benzene molar ratio in the dehydrogenation reactor. The process results in a long life of the dehydrogenation catalyst due to reduced coking.

25 Claims, 1 Drawing Sheet

CYCLOHEXANE DEHYDROGENATION

PRIORITY CLAIM TO RELATED APPLICATIONS

This application is a National Stage Application of International Application No. PCT/US2013/072539 filed Dec. 2, 2013, which claims priority to U.S. Provisional Application Ser. No. 61/733,732 filed Dec. 5, 2012, and European Application No. 13154528.7 filed Feb. 8, 2013, the disclosures of which are fully incorporated herein by their reference.

FIELD

The present invention relates to a process for dehydrogenating cyclohexane. In particular, the present invention relates to a process for dehydrogenating cyclohexane to make benzene. The present invention is useful, e.g., in making cyclohexylbenzene via benzene hydroalkylation.

BACKGROUND

Various dehydrogenation processes have been proposed to dehydrogenate non-aromatic six membered ring compounds. These dehydrogenation processes are typically used to convert non-aromatic compounds such as cyclohexane into aromatic compounds such as benzene wherein the aromatic compound produced may be used as a raw material in a subsequent process. Alternatively, the aromatic compound produced may be used as a raw material in the same process which produced the non-aromatic compound to be dehydrogenated. For example, the dehydrogenation of cyclohexane to benzene can be important in the hydroalkylation process for producing cyclohexylbenzene as illustrated below.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene, which then alkylates the benzene starting material. In this regard, U.S. Pat. No. 6,037,513 has disclosed that cyclohexylbenzene selectivity in the hydroalkylation of benzene can be improved by contacting the benzene and hydrogen with a bifunctional catalyst comprising of at least one hydrogenation metal and a molecular sieve of the MCM-22 type. The hydrogenation metal is preferably selected from palladium, ruthenium, nickel, cobalt, and mixtures thereof and the contacting step is conducted at a temperature of about 50° C. to 350° C., a pressure of about 100 kPa to 7000 kPa, a hydrogen to benzene molar ratio of about 0.01 to 100 and a weight hourly space velocity (WHSV) of about 0.01 hr$^{-1}$ to 100 hr$^{-1}$. This reference discloses that the resultant cyclohexylbenzene can then be oxidized to the corresponding hydroperoxide and the peroxide decomposed to the desired phenol and cyclohexanone. Nonetheless, notwithstanding the high selectivity of the hydroalkylation reaction over the MCM-22 molecular sieve-based bifunctional catalyst in the disclosed method, certain amounts of cyclohexane and methylcyclopentane are produced in the hydroalkylation effluent.

Production of impurities such as cyclohexane and methylcyclopentane represent loss of valuable benzene feed. The overall benzene conversion rates are typically only 40 wt % to 60 wt %. Therefore, recycle of unreacted benzene is desired. Unless removed, these impurities including cyclohexane and methylcyclopentane will tend to build up in the recycle stream thereby displacing benzene and increasing the production of undesirable by-products. Thus, a significant problem facing the commercial application of cyclohexylbenzene as a phenol precursor is removing the cyclohexane in the benzene recycle streams.

One solution to this problem is proposed in U.S. Pat. No. 7,579,511, which describes a process for making cyclohexylbenzene in which benzene undergoes hydroalkylation in the presence of a hydroalkylation catalyst to form a first effluent stream containing cyclohexylbenzene, cyclohexane, methylcyclopentane, and unreacted benzene. The first effluent stream is then separated into a cyclohexane/methylcyclopentane-rich stream, a benzene-rich stream, and a cyclohexylbenzene-rich stream and the cyclohexane/methylcyclopentane-rich stream is contacted with a second, low acidity, dehydrogenation catalyst to convert at least a portion of the cyclohexane to benzene and at least a portion of the methylcyclopentane to linear and/or branched paraffins and form a second effluent stream. The benzene-rich stream and the second effluent stream can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a hydroalkylation catalyst to produce a first effluent stream containing cyclohexylbenzene, cyclohexane, and unreacted benzene. The first effluent stream is then divided into a cyclohexylbenzene-rich stream and a $C_6$ product stream comprising cyclohexane and benzene. At least part of the $C_6$ product stream is then contacted with a second catalyst under dehydrogenation conditions to convert at least part of the cyclohexane to benzene and produce a second effluent stream which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group 8, 9, or 10 metal on a porous inorganic support such as aluminum oxide, silicon oxide, titanium oxide, zirconium oxide, activated carbon, and combinations thereof. WO11/096991 (2010EM139) further discloses a dual-component catalyst system for the dehydrogenation reaction.

SUMMARY

In the dehydrogenation reaction of cyclohexane, the following Reaction-1 occurs:

(Reaction-1)

It has been found that in the above reaction, if cyclohexane is fed into the dehydrogenation reactor in the absence of benzene and hydrogen, side reactions occur, leading to formation of undesirable products which coke and deactivate the catalyst quickly. The problem of side reactions is exacerbated if the feed supplied into the dehydrogenation reaction comprises a non-negligible amount of methylcyclopentane. The methylcyclopentane present in the feed can undergo dehydrogenation reactions to produce a series of intermediate compounds, such as methylcyclopentene, which are prone to producing coking materials that can deactivate the catalyst quickly. As such, it is highly desirable that the dehydrogenation feed comprises, in addition to cyclohexane, benzene and hydrogen, and the molar ratio of hydrogen to benzene be controlled.

The present invention provides a convenient method for controlling the partial pressure of benzene, hence molar ratio of benzene to hydrogen, in the dehydrogenation feed by obtaining the benzene feed from the vapor phase of temperature-controlled condensation separation system.

A first aspect of the present application relates to a process for dehydrogenating cyclohexane, the process comprising:

(1A) obtaining a benzene-containing stream from a vapor phase at a vapor outlet of a condensation separation system, wherein the vapor phase is in equilibrium with a liquid phase in the condensation separation system and has a controlled partial pressure of benzene;

(1B) supplying benzene, hydrogen, and cyclohexane into a dehydrogenation reactor, where at least a portion of the benzene is supplied from the benzene-containing stream; and (1C) contacting at least a portion of the cyclohexane with a dehydrogenating catalyst in the reactor under a dehydrogenation condition to produce a dehydrogenation effluent.

A second aspect of the present disclosure relates to a process for process for making cyclohexylbenzene, the process comprising:

(2A) contacting benzene with hydrogen in the presence of a hydroalkylation catalyst under a hydroalkylation condition to produce a hydroalkylation effluent comprising benzene, cyclohexylbenzene, cyclohexane, and hydrogen;

(2B) separating at least a portion of the hydroalkylation effluent to produce a first fraction comprising cyclohexylbenzene at a higher concentration than the hydroalkylation effluent and a second fraction comprising benzene, cyclohexane, and hydrogen;

(2C) separating at least a portion of the second fraction in a condensation separation system into a liquid phase and a vapor phase in equilibrium with the liquid phase, where the partial pressure of benzene in the vapor phase is controlled;

(2D) supplying the vapor phase from the condensation separation system into a dehydrogenation reactor; and (2E) contacting at least a portion of the cyclohexane in the vapor phase with a dehydrogenation catalyst in the dehydrogenation reactor under a dehydrogenation condition to produce a dehydrogenation effluent comprising benzene and hydrogen.

A third aspect of the present disclosure relates to a process for making phenol and/or cyclohexanone, the process comprising:

(3A) producing cyclohexylbenzene according to a process of the second aspect;

(3B) oxidizing at least a portion of the cyclohexylbenzene to obtain cyclohexylbenzene hydroperoxide; and (3C) subjecting at least a portion of the cyclohexylbenzene hydroperoxide to a cleavage reaction to obtain a cleavage reaction effluent comprising phenol and cyclohexanone.

The processes of the present disclosure can have at least some of the following advantages. First, by using a condensation separation system capable of controlling the temperature of the vapor phase, the partial pressure of benzene in the vapor supplied to the dehydrogenator can be precisely and conveniently controlled; Second, the invention enable one to monitor the hydrogen to benzene molar ratio in the feed to the dehydrogenator closely and adjust the ratio accordingly to avoid coking conditions in the reactor; and Third, the use of expensive hydrogen supply and controlled equipment, such as compressors can be avoided.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more, or even all steps, may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, steps are performed in the order listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with MCM-22 type molecular sieves. Desirably, the molecular sieve is selected from (a) MCM-49, (b) MCM-56, and (c) isotypes of MCM-49 and MCM-56, such as ITQ-2.

In the processes according to the present disclosure, cyclohexane, benzene, and hydrogen are supplied to the cyclohexane dehydrogenation reactor. At least a portion of the cyclohexane, hydrogen, and benzene can be supplied in a combined stream. Alternatively, cyclohexane, benzene, and hydrogen are supplied via separate inlets in separate streams into the reactor. Before contacting the dehydrogenation catalyst, it is highly desired that these components mix to form a substantially homogeneous gas, and the dehydrogenation reactor occurs in a gaseous phase. Upon contacting the catalyst, the cyclohexane is converted into benzene in a highly endothermal reaction while releasing hydrogen. While the introduction of benzene and hydrogen would shift the equilibrium of the dehydrogenation reaction toward cyclohexane, the presence of benzene and hydrogen was found necessary for an acceptable conversion and life of the catalyst. This is because, without the presence of hydrogen, a number of side reactions may occur resulting in intermediates (such as methylcyclopentane, methylcyclopentane, and methylcyclopentadiene) prone to forming coke that can deactivate the dehydrogenation catalyst quickly. Benzene in the feed would shift the reaction towards cyclohexane, thereby lowering the conversion to a small extent. However, the presence of benzene is beneficial in that it acts as a heat carrier providing the high temperature required for a converting a desirable proportion of cyclohexane into benzene, which significantly outweigh the negative impact on the chemical equilibrium due to an elevated benzene concentration in the reaction medium.

The feed supplied to the dehydrogenation reactor, including benzene and/or cyclohexane, may comprise a non-negligible amount of methylcyclopentane. For example, in a typical benzene hydroalkylation process for making cyclohexylbenzene, in addition to unreacted benzene, cyclohexane and cyclohexylbenzene, methylcyclopentane at a concentration of from 100 ppm to 5 wt % may be present in the effluent, based on the total weight of benzene, cyclohexane, and methylcyclopentane. In order to increase the overall productivity of the process, the unreacted benzene, cyclohexane and methylcyclopentane may be separated from the heavier cyclohexylbenzene, subjected to dehydrogenation where cyclohexane is converted into benzene, optionally purified, and then recycled to the benzene hydroalkylation step. It has been found that the methylcyclopentane present in the mixture of benzene and cyclohexane can be particularly detrimental to the performance, including conversion and life, of the dehydrogenation catalyst. Without intending to be bound by a particular theory, it is believed that methylcyclopentane can be dehydrogenated into methylcyclopentene and methycyclopentadiene, which can form coking compounds that can deactivate the dehydrogenation catalyst. The catalyst-deactivating effect of methylcyclopentane can be dramatic, even at a relatively low concentration, if hydrogen is not present at a sufficient concentration in the dehydrogenation reactor. The presence of hydrogen at a desirable concentration can inhibit the dehydrogenation of methylcyclopentane, hence the formation of coking products.

Thus, it is desired that that the molar ratio of hydrogen to benzene inside the dehydrogenation reactor is controlled in a range from Rhb1 to Rhb2, where Rhb1 can be 0.2, 0.4, 0.6, 0.8, 1.0, 1.2, 1.4, 1.5, 1.6, 1.8, 2.0, 2.5, or 3.0, and Rhb2 can be 6.0, 5.8, 5.6, 5.4, 5.2, 5.0, 4.8, 4.6, 4.4, 4.2, 4.0, 3.5, or 3.0, as long as Rhb1<Rhb2. Where methylcyclopentane is present in the feed material, it is highly desired that the molar ratio of hydrogen to benzene in the dehydrogenation reactor is from 1.0 to 3.0, such as from 1.5 to 2.5.

For example, the absolute partial pressure of hydrogen in the atmosphere inside the dehydrogenation reactor can be maintained in a range from P1 kPa to P2 kPa, where P1 can be 60, 70, 80, 90, 100, 120, 140, 150, 160, 180, 200, 220, 240, 260, 280, 300, 350, 400, 450, or 480; and P2 can be 800, 780, 760, 740, 720, 700, 680, 660, 640, 620, 600, 580, 560, 540, 520, or 500. It is highly desirable to maintain the absolute partial pressure of hydrogen in the total feed material substantially stable, such that the variation thereof is within ΔP kPa, where ΔP can be 50, 45, 40, 35, 30, 25, 20, 15, 10, 8, 6, 5, 4, 3, or even 2.

To control the total pressure of the gas fed into the dehydrogenation reactor, it is advantageous and convenient to control the total pressure of the vapor phase at the vapor outlet of the condensation separation system, especially if the total feed stream is supplied from the vapor phase of the condensation separation system. Thus, the average of the total absolute pressure at the vapor outlet of the condensation separation system may be controlled within a range from P1 kPa to P2 kPa, where P1 can be: 100, 110, 120, 130, 140, 150, 160, 170, or 180; and P2 can be: 300, 290, 280, 270, 260, 250, 240, 230, 220, 210, or 200. It is highly desirable to maintain the absolute total pressure at the vapor outlet of the condensation separation system substantially stable, such that the variation thereof is within ΔP1 kPa, where ΔP1 can be 50, 45, 40, 35, 30, 25, 20, 15, 10, 8, 6, 5, 4, 3, or even 2.

The dehydrogenation reaction of cyclohexane to produce benzene is endothermic. As such, the higher the temperature, the more favorable for the production of benzene. However, if the temperature is too high, side reactions tend to become more pronounced, resulting in the production of more coke that can poison the dehydrogenation catalyst quickly. As such, it is desired that the feed materials, including benzene, hydrogen, and cyclohexane, are heated to a dehydrogenation temperature in a range from T1° C. to T2° C., where T1 can be: 350, 360, 370, 380, 390, 400, 410, 420, 430, 440, or 450; and T2 can be 550, 540, 530, 520, 510, 500, 490, 480, 470, 460, 450; as long as T1<T2. Given the endothermic nature of the reaction, the dehydrogenation effluent may exhibit a temperature lower than the feed materials by ΔT° C., where ΔT can be: 100, 90, 80, 70, 60, 50, 40, or even 30.

In the processes according to the present disclosure, at least a portion of the benzene fed into the dehydrogenation reactor in step (1B) is provided from a vapor phase at a vapor outlet of a condensation separation system, where the vapor phase is at phase equilibrium with a liquid phase. A condensation separation system is a system comprising a heat exchanger, called condenser, where a vapor-containing material is subjected to cooling and allowed to condense to produce at least part of the liquid phase. The condensation separation system can be a condenser, where the cooling and separation occur in the same vessel, and the vapor phase exits from the condenser at its vapor outlet. The condensation separation system may comprise a condenser producing a vapor/liquid mixture from a vapor feed, and a vapor-liquid separation drum that separate the vapor/liquid mixture into a vapor phase exiting at a vapor outlet and a liquid phase exiting at a liquid outlet. At equilibrium temperature, the amount of vapor condensed to form liquid equals the amount of vapor produced as a result of vaporization of the liquid phase. In the processes of the present disclosure, the temperature of the vapor outlet of the condensation separation system is such that benzene is at equilibrium in both the vapor and liquid phases. By controlling the temperature of the vapor outlet in direct contact with the vapor and liquid phases, one can control the absolute partial pressure of benzene in the vapor phase at a given total overall system pressure thereof in the condensation separation system, hence the partial pressure of benzene fed into the dehydrogenation reactor, and eventually, the molar ratio of hydrogen to benzene in the materials fed into the dehydrogenation reactor, thereby avoiding dehydrogenation conditions causing coking and catalyst deactivation.

Control of the temperature of the vapor phase of the condensation separation system can be achieved by adjusting the flow rate or temperature of the cooling medium passing through the condenser, or by directing a quantity of the process fluid from the inlet of the condensation separation system to the vapor phase in the condenser close to the vapor outlet, or to the vapor phase of the separation drum of the condensation separation system, effectively bypassing a part, or the entirety, of the condenser. The cooling operations of the condensation separation system can be controlled by a feedback loop including a temperature sensor such as a thermocouple for measuring the outlet temperature, and an electrical controller such as a computer system connected to the cooling means. From the measured temperature of the vapor outlet, one would be able to conveniently determine the benzene partial pressure in the vapor fed to the dehydrogenation reactor.

The variation of the temperature of the vapor phase (and the vapor outlet of the condensation separation system) can be controlled within ΔTo° C., where ΔTo can be: 20, 18, 16, 15, 14, 12, 10, 8, 6, 5, 4, or even 3.

The materials fed into the dehydrogenation reactor may be supplied from multiple sources. For example, benzene alone can be supplied from a vapor outlet of a condensation separation system, while hydrogen and cyclohexane can be supplied from separate sources, and the three components can be mixed inside the dehydrogenation reactor before they are allowed to contact the dehydrogenation catalyst. Preferably, however, all of the hydrogen, benzene, and cyclohexane are supplied from a single vapor outlet of a single condensation separation system.

Step (1A) of the process according to the present disclosure may preferably comprise:

(1A-I) producing a material stream comprising benzene, cyclohexane, and hydrogen;

(1A-II) separating the material stream into the liquid phase and the vapor phase in the condensation separation system in equilibrium with the liquid phase; and (1A-III) supplying the vapor phase at the vapor outlet to the dehydrogenation reactor.

The vapor phase thus may comprise benzene, cyclohexane, and hydrogen. As indicated above, the benzene partial pressure in the vapor phase supplied to the dehydrogenation reactor is then determined by the temperature of the outlet in direct contact with the vapor phase and the liquid phase in equilibrium, as well as the overall pressure of the mixture. Likewise, the cyclohexane partial pressure in the vapor phase supplied to the dehydrogenation reactor is determined by the same temperature. In a condensation separation system comprising a liquid/vapor separation drum, the temperature of the liquid/vapor inside the drum would then determine substantially the partial pressures of both benzene and cyclohexane in the vapor phase supplied to the dehydrogenation reactor for a material stream with a given composition. Typically, the vapor outlet is an integral part of the drum or the condenser, and therefore would have the same temperature of the drum and/or the part of the condenser in direct contact with the vapor taken away from the system in equilibrium with the liquid. Given a predetermined $H_2$ partial pressure in the material system, which can be precisely and reliably controlled, and the composition of the material stream, one can precisely determine the benzene/$H_2$ molar ratio and cyclohexane/$H_2$ molar ratio in the vapor stream fed into the dehydrogenation reactor.

The vapor phase in step (1A-III) may further comprise methylcyclopentane at a concentration in a range from 100 ppm to 5 wt %, based on the total weight of benzene, cyclohexane, and methylcyclopentane. Specifically, step (1A-I) may comprise:

(1A-I-1) contacting benzene with hydrogen in the presence of a hydroalkylation catalyst under a hydroalkylation condition to produce a hydroalkylation effluent comprising benzene, cyclohexane, hydrogen and cyclohexylbenzene;

(1A-I-2) separating at least part of the hydroalkylation effluent to produce a first fraction comprising cyclohexylbenzene at a concentration higher than the hydroalkylation effluent and a second fraction comprising benzene, cyclohexane, and hydrogen; and (1A-I-3) obtaining the material stream comprising benzene, cyclohexane, and hydrogen from the second fraction.

It is known that in step (1A-I-1), methylcyclopentane may be produced and result in methylcyclopentane concentration in a range of 100 ppm to 5 wt % in the materials supplied to the dehydrogenation reactor, based on the total weight of cyclohexane, benzene, and methylcyclopentane.

Because the dehydrogenation reaction of cyclohexane produces a significant amount of hydrogen, the concentration of hydrogen in the dehydrogenation effluent is higher than in the materials supplied to the dehydrogenation reactor. The hydrogen in the dehydrogenation effluent may be separated, cleaned and then recycled to the hydroalkylation step (1A-I-1). The hydrogen may be cleaned, by pure benzene. Likewise, the benzene present in the dehydrogenation effluent may be recycled to the hydroalkylation step (1A-I-1) to increase the overall yield of cyclohexylbenzene in the process. Because the boiling points of benzene and cyclohexane are quite similar, separation of them may be uneconomical. Cyclohexane is largely inert in the hydroalkylation step (1A-I-1). As such, both of the benzene and cyclohexane present in the dehydrogenation effluent may be partly recycled to the hydroalkylation step without separation. The benzene and cyclohexane may be distilled to remove impurities such as toluene, C12, and the like, before being recycled to the hydroalkylation step.

The second aspect of the present disclosure, relating to a process for making cyclohexylbenzene, can be readily understood by referring to the above description of the various steps of the process of the first aspect in relation to the benzene hydroalkylation.

The third aspect of the present disclosure, relating to a process for making phenol, can be readily understood by referring to the above description of the second aspect and the first aspect and the following detailed description of a specific example for making phenol and cyclohexanone via cyclohexylbenzene.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-2 to produce cyclohexylbenzene (CHB):

(Reaction-2)

For an example of hydroalkylation of benzene in the presence of hydrogen for the production of cyclohexylbenzene, see U.S. Pat. Nos. 6,730,625 and 7,579,511, which are incorporated by reference. Also, see International Application Publications WO2009/131769 or WO2009/128984, directed to catalytic hydroalkylation of benzene in the presence of hydrogen for the production of cyclohexylbenzene.

The catalyst employed in the hydroalkylation reaction is a bifunctional catalyst comprising a molecular sieve of the MCM-22 type and a hydrogenation metal, described above.

Any known hydrogenation metal may be employed in the hydroalkylation catalyst, although suitable metals include palladium, ruthenium, nickel, zinc, tin, and cobalt, with palladium being particularly advantageous. Desirably, the amount of hydrogenation metal present in the catalyst is between 0.05 wt % and 10 wt %, such as between 0.10 wt % and 5 wt %, of the catalyst.

Suitable binder materials include synthetic or naturally occurring substances as well as inorganic materials such as clay, silica, and/or metal oxides.

Although the hydroalkylation reaction is highly selective towards cyclohexylbenzene, the effluent from the hydroalkylation reaction may contain cyclohexane, some dialkylated products, as well as unreacted benzene and the desired monoalkylated species. The unreacted benzene may be recovered by distillation and recycled to the alkylation reactor. The lower effluent from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species. The cyclohexane may be dehydrogenated according to the processes of the present disclosure to form benzene and hydrogen, which may be recycled to the hydroalkylation step.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene is fed to the oxidation reaction.

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

Regardless of the source(s), a feed comprising cyclohexylbenzene may contain at least 10 wt %, or at least 25 wt %, or at least 50 wt %, or at least 65 wt %, or at least 75 wt %, or at least 95 wt %, or at least 99 wt % cyclohexylbenzene. The feed comprising cyclohexylbenzene may further contain: (i) at least 1 ppm and no greater than 1 wt % bicyclohexane, or at least 10 ppm and no greater than 8000 ppm bicyclohexane; (ii) at least 1 ppm and no greater than 1 wt %, or at least 10 ppm and no greater than 8000 ppm, biphenyl; and (iii) at least 1 ppm and no greater than 2 wt % methylcyclopentylbenzene, or at least 10 ppm and no greater than 1 wt % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, e.g., no greater than 1000 ppm, or no greater than 100 ppm of phenol, olefins or alkylene benzenes such as cyclohexenyl benzene, individually or in any combination. The feed comprising cyclohexylbenzene to which oxygen is introduced to cause an oxidation reaction may contain cyclohexylbenzene, any other one component, or any combination of the other components just noted in the proportions for each or in combination just noted.

Oxidation may be accomplished by contacting an oxygen-containing gas, such as air and various derivatives of air, with the feed comprising cyclohexylbenzene.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI).

The oxidation reaction occurs under suitable oxidation conditions including, e.g., a temperature between 70° C. and 200° C., such as 90° C. to 130° C., and a pressure of 50 kPa to 10,000 kPa. A basic buffering agent may be added to react with acidic by-products that may form during the oxidation. In addition, an aqueous phase may be introduced. The reaction may take place in a batch or continuous flow fashion.

Desirably, the product of the oxidation of a feed comprising cyclohexylbenzene, i.e., the oxidation composition, contains at least 5 wt %, such as at least 10 wt %, for example at least 15 wt %, or at least 20 wt % cyclohexyl-1-phenyl-1-hydroperoxide based upon the total weight of the oxidation composition. In other manifestations, the oxidation composition contains no greater than 80 wt %, no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. The reactor used for the oxidation of cyclohexylbenzene, i.e., the oxidation reactor, may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel container with a distributor inlet for the oxygen-containing stream in line. The oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. The oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition as directly produced may undergo one or more separations, and an appropriate product of that separation (or separations), now modified in composition relative the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then, likely requires high temperatures that could cause uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which may then be separated either by filtration or by scraping from a heat exchanger surface used to effect the crystallization, and provide at least a portion of the oxidation composition reduced, or free from, imide oxidation catalyst that may be subjected to a cleavage reaction.

As another example, all or a fraction of the oxidation composition as produced may be subjected to water washing and then passage through an adsorbent, such as a 3 Å molecular sieve, to separate water and other adsorbable compounds, and provide at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide an at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or hydrogen carbonate, to form an aqueous phase comprising a salt of the imide oxidation catalyst, and an organic phase reduced in imide oxidation catalyst provided as an at least a portion of the oxidation composition that may be subjected to a cleavage reaction.

Cleavage Reaction

As discussed above, the process includes cleaving at least a portion of the oxidation composition in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

The acid catalyst may be at least partially soluble in the cleavage reaction mixture, stable at a temperature of at least 185° C. and has a lower volatility (higher normal boiling point) than cyclohexylbenzene. The acid catalyst can be also at least partially soluble in the treated cleavage reaction mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction mixture may contain at least 50 weight-parts-per-million (ppm) and no greater than 3000 ppm of the acid catalyst, or at least 150 ppm to and no greater than 2000 ppm of the acid catalyst, or at least 300 ppm and no greater than 1500 ppm of the acid catalyst, based upon total weight of the cleavage reaction mixture.

The cleavage reaction mixture can include cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

The cleavage reaction occurs under suitable cleavage conditions including, e.g., a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, may be high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone, each of which may comprise 40 wt % to 60 wt %, or 45 wt % to 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 wt % and no greater than 10 wt %, or at least 0.5 wt % and no greater than 7 wt %, or at least 1 wt % and no greater than 5 wt %, or at least 1.5 wt % and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is, anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone, or unconverted cyclohexylbenzene, or some combination thereof. A contaminant in the cleavage reaction mixture or the neutralized cleavage mixture or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor can comprise a plurality of reactors in series, each performing a portion of the conversion reaction, optionally operating in different modes and at different conditions selected to enhance the cleavage reaction at the pertinent conversion range. The cleavage reactor can include a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can remove at least part of the heat generated in the reaction.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

DESCRIPTION ACCORDING TO THE DRAWINGS

Figure 1:
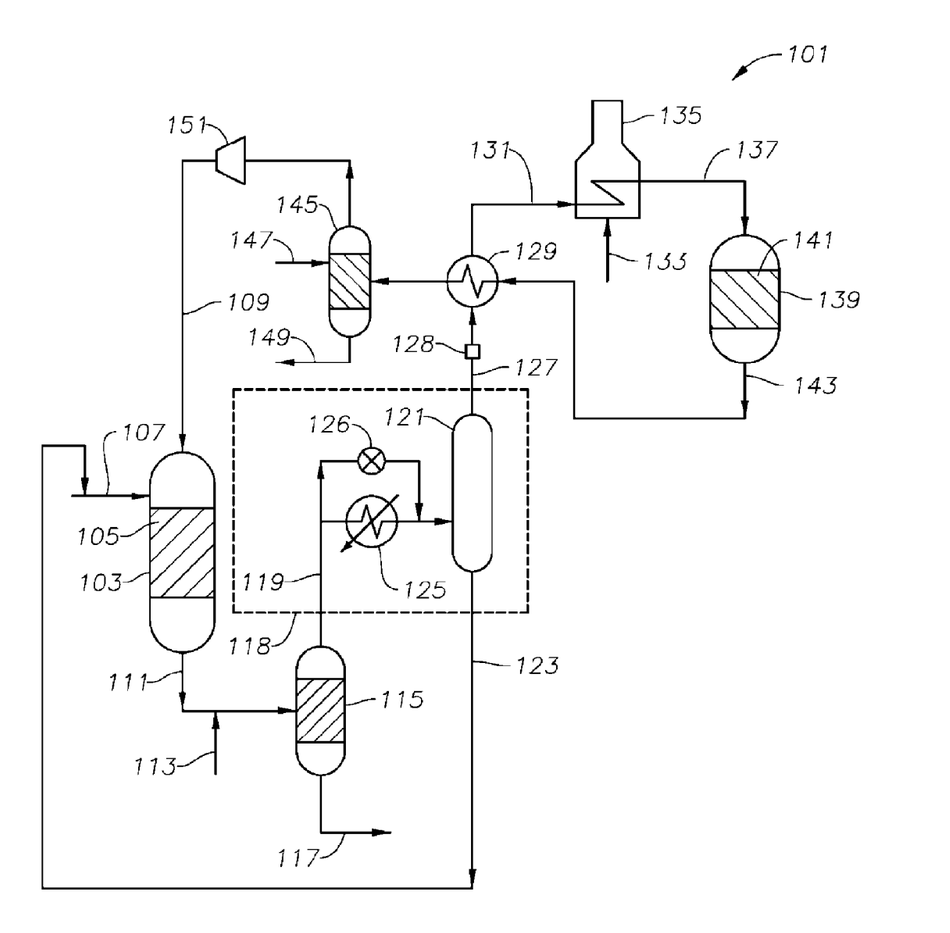
FIG. 1 is a schematic diagram showing an exemplary process for making cyclohexylbenzene according to the present disclosure.

FIG. 1 schematically illustrates a system 101 for making cyclohexylbenzene according to one exemplary process of the present disclosure. In this system, a feed stream 107 comprising benzene and a clean hydrogen stream 109 are fed into a hydroalkylation reactor 103. Inside the reactor 103, they form a reaction mixture, flow downwards to contact a bed of hydroalkylation catalyst 105 comprising Pd and a molecular sieve of the MCM-22 type and $Al_2O_3$ binder, react to form a hydroalkylation reaction effluent 111. The effluent 111, optionally together with a make-up hydrogen stream 113, is delivered into a fractionation distillation column 115, where a liquid bottoms effluent 117 comprising C12 such as cyclohexylbenzene and a top effluent 119 comprising hydrogen, benzene, cyclohexane and methylcyclopentane are produced. The effluent 119 is then delivered to condensation separation system shown as a dotted-line enclosure 118 comprising a condenser 125, a by-passing line having an adjustable valve 126, and a liquid/vapor separation drum 121 for receiving the liquid and vapor phases flowing from the condenser 125 and the bypassing line, where a liquid phase 123 and vapor phase 127 are produced in equilibrium at the vapor outlet 128 directly connected with the drum 121. The liquid phase, comprising both benzene and cyclohexane, is recycled back to the hydroalkylation reactor 103 as part of the feed stream 107. A thermometer such as a thermocouple can be installed at the outlet 128 to measure the temperature of the vapor phase 127. As discussed above, for a given total pressure of vapor phase 127 comprising benzene and a given composition of material stream 119, the partial pressures of benzene and cyclohexane are determined by the measured temperature of the vapor phase at the vapor outlet 128. Thus, deviation of the measured temperature at 128 can be translated into deviation of the partial pressures from target values. If the measured temperature is too high, one can lower the temperature of the cooling medium of the condenser 125, or reduce the amount of the bypassing stream by adjusting the valve 126, and vice versa. Thus, precise monitoring and control of the partial pressures of benzene, cyclohexane, and the molar ratios of benzene/$H_2$ and cyclohexane/$H_2$ can be achieved using this design. The vapor phase 127 is then heated at a heat exchanger 129 by the dehydrogenation effluent 143, further heated at a furnace 135 which burns a stream of natural gas 133, to form a gas stream 137 with a temperature in a range from 400° C. to 550° C., and delivered to the dehydrogenation reactor 139, where contact with the bed of dehydrogenation catalyst 139 converts cyclohexane to benzene and hydrogen. The dehydrogenation effluent 143, at a lower temperature than the stream 137, passes the heat exchanger 129, where it is cooled down by the stream 127, before being fed into a scrubber column 145, where the hydrogen gas is cleaned by a fresh, clean stream of benzene 147. The clean hydrogen gas stream can be delivered via a compressor 151 into the hydroalkylation reactor 103 as the clean hydrogen supply 109.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references described herein are incorporated by reference in their entirety.

Non-limiting embodiments of the processes of the present disclosure include:

E1. A process for dehydrogenating cyclohexane, the process comprising:

(1A) obtaining a benzene-containing stream from a vapor phase at a vapor outlet of a condensation separation system, wherein the vapor phase is in equilibrium with a liquid phase in the condensation separation system and has a controlled partial pressure of benzene;

(1B) supplying benzene, hydrogen, and cyclohexane into a dehydrogenation reactor, wherein at least a portion of the benzene is supplied from the benzene-containing stream; and (1C) contacting at least a portion of the cyclohexane with a dehydrogenating catalyst in the reactor under a dehydrogenation condition to produce a dehydrogenation effluent.

E2. The process of E1, wherein step (1B) further comprises supplying methylcyclopentane into the dehydrogenation reactor at a concentration from 100 ppm to 5 wt %, based on the total weight of benzene, cyclohexane, and methylcyclopentane.

E3. The process of E1 or E2, wherein step (1B) comprises supplying at least a portion of the benzene, a portion of the hydrogen, and a portion of the cyclohexane in a single stream to the dehydrogenation reactor.

E4. The process of E3, wherein step (1B) comprises supplying all of the benzene, all of the hydrogen, and all of the cyclohexane and optionally methylcyclopentane via the benzene-containing stream provided in step (1A) into the dehydrogenation reactor.

E5. The process of E4, wherein the benzene-containing stream is supplied from a single vapor outlet of a single condensation separation system.

E6. The process of any of E1 to E5, wherein the condensation separation system is a condenser.

E7. The process of any of E1 to E6, wherein the temperature of the vapor existing the condensation separation system is controlled by controlling the temperature and/or flow rate of a cooling medium in the condenser.

E8. The process of any of E1 to E7, wherein the condensation separation system comprises a condenser and a separation drum.

E9. The process of E8, wherein the temperature of the vapor existing the condensation separation system is controlled by directing a quantity of a fluid to be fed into the condenser to the separation drum.

E10. The process of any of E1 to E9, wherein in step (1B) the molar ratio of hydrogen to benzene in the dehydrogenation reactor is controlled within a range from 0.2 to 4.

E11. The process of any of E1 to E10, wherein in step (1B) the partial pressure of hydrogen in the dehydrogenation reactor is maintained in a range from 60 to 1400 kPa.

E12. The process of any of E1 to E11, wherein in step (1B) the variation of the total absolute pressure at the vapor outlet of the condensation separation system is controlled within 50 kPa.

E13. The process of any of E1 to E12, wherein in step (1B) the average of the total absolute pressure at the vapor outlet is in a range from 100 kPa to 1750 kPa (4:1 ratio of $H_2$).

E14. The process of any of E1 to E13, wherein the dehydrogenation condition comprises a temperature in a range from 350° C. to 550° C.

E15. The process of any of E1 to E14, wherein the temperature of the vapor exiting the condensation separation system is controlled within a range from 40° C. to 170° C.

E16. The process of E15, wherein the variation of the temperature of the vapor exiting the condensation separation system is controlled within 20° C.

E17. The process of any of E1 to E16, wherein step (1A) comprises:
(1A-I) producing a material stream comprising benzene, cyclohexane and hydrogen;
(1A-II) separating the material stream into the liquid phase and the vapor phase in equilibrium in the condensation separation system; and
(1A-III) providing the benzene-containing stream from the vapor phase.

E18. The process of E17, wherein in step (1A-I), the material stream further comprises methylcyclopentane, and in step (1A-III), the vapor phase further comprises methylcyclopentane at a concentration in a range from 100 ppm to 5 wt %, based on the total weight of benzene, cyclohexane, and methylcyclopentane in the vapor phase.

E19. The process of E17 or E18, wherein step (1A-I) comprises:
(1A-I-1) contacting benzene with hydrogen in the presence of a hydroalkylation catalyst under a hydroalkylation condition to produce a hydroalkylation effluent comprising benzene, cyclohexane, hydrogen, and cyclohexylbenzene;
(1A-I-2) separating at least a portion of the hydroalkylation effluent to produce a first fraction comprising cyclohexylbenzene at a higher concentration than the hydroalkylation effluent and a second fraction comprising benzene, cyclohexane, and hydrogen; and
(1A-I-3) obtaining the material stream comprising benzene, cyclohexane, and hydrogen from the second fraction.

E20. The process of E19, wherein in step (1A-I-1), the hydroalkylation effluent further comprises methylcyclopentane, and in step (1A-I-3), the material stream further comprises methylcyclopentane at a concentration in a range from 100 ppm to 5 wt %, based on the total weight of benzene, cyclohexane, and methylcyclopentane therein.

E21. The process of E19 or E20, further comprising recycling at least a portion of the hydrogen in the dehydrogenating effluent to the contacting step (1A-I-1).

E22. The process of any of E17 to E21, further comprising recycling at least a portion of the benzene in the dehydrogenating effluent to the contacting step (1A-I-1).

E23. The process of any of E17 to E21, further comprising recycling at least a portion of the dehydrogenating effluent comprising both benzene and cyclohexane to the contacting step (1A-I-1).

E24. A process for making cyclohexylbenzene, the process comprising:
(2A) contacting benzene with hydrogen in the presence of a hydroalkylation catalyst under a hydroalkylation condition to produce a hydroalkylation effluent comprising benzene, cyclohexylbenzene, cyclohexane, and hydrogen;
(2B) separating at least a portion of the hydroalkylation effluent to produce a first fraction comprising cyclohexylbenzene at a higher concentration than the hydroalkylation effluent and a second fraction comprising benzene, cyclohexane, and hydrogen;
(2C) separating at least a portion of the second fraction in a condensation separation system into a liquid phase and a vapor phase in equilibrium with the liquid phase;
(2D) supplying the vapor phase at the vapor outlet from the condensation separation system into a dehydrogenation reactor to obtain a reaction medium; and
(2E) contacting at least a portion of the cyclohexane in the reaction medium with a dehydrogenation catalyst in the dehydrogenation reactor under a dehydrogenation condition to produce a dehydrogenation effluent comprising benzene and hydrogen.

E25. The process of E24, wherein in step (2A), the hydroalkylation effluent further comprises methylcyclopentane, and in step (2D), the vapor phase comprises methylcyclopentane at a concentration in a range from 100 ppm to 5 wt %, based on the total weight of benzene, cyclohexane, and methylcyclopentane in the reaction medium.

E26. The process of E24 or E25, the process further comprising:
(2F) recycling at least a portion of the benzene and/or the hydrogen contained in the dehydrogenation effluent from step (2E) to the contacting step (2A).

E27. The process of any of E24 to E26, wherein in step (2C), the partial pressure of hydrogen is controlled within a range from 5 kPa to 300 kPa.

E28. The process of any of E24 to E27, wherein in step (2C), the partial pressure of benzene is controlled by controlling the temperature of the vapor exiting the condensation separation system within a range from 40° C. to 170° C.

E29. The process of E28, wherein in step (2C), the variation of the temperature of the vapor exiting the condensation separation system is controlled within 20° C.

E30. The process of any of E24 to E29, wherein in step (2E), the dehydrogenation condition comprises at least one of:

(a) a temperature of the reaction medium in the dehydrogenation reactor in a range from 350° C. to 550° C.; and (b) an absolute pressure in the dehydrogenation reactor in a range from 60 to 800 kPa.

E31. The process of any of E24 to E30, wherein in step (2E), the dehydrogenation catalyst comprises a group 8-10 metal supported on an oxide substrate.

E32. The process of any of E24 to E31, wherein in step (2E), the dehydrogenation catalyst comprises an oxide support and a Group 8-10 metal.

E33. A process for making phenol and/or cyclohexanone, the process comprising:

(3A) producing cyclohexylbenzene in a process according to any of E24 to E32;

(3B) oxidizing at least a portion of the cyclohexylbenzene to obtain cyclohexylbenzene hydroperoxide; and (3E) subjecting at least a portion of the cyclohexylbenzene hydroperoxide to a cleavage reaction to obtain a cleavage reaction effluent comprising phenol and cyclohexanone.

The invention claimed is:

1. A process for dehydrogenating cyclohexane, the process comprising:

(1A) obtaining a benzene-containing stream from a vapor phase at a vapor outlet of a condensation separation system, wherein the vapor phase is in equilibrium with a liquid phase in the condensation separation system and has a controlled partial pressure of benzene;

(1B) supplying benzene, hydrogen and cyclohexane into a dehydrogenation reactor, wherein at least a portion of the benzene is supplied from the benzene-containing stream; and (1C) contacting at least a portion of the cyclohexane with a dehydrogenation catalyst in the reactor under a dehydrogenation condition to produce a dehydrogenation effluent;

wherein the molar ratio of hydrogen to benzene in the dehydrogenation reactor is controlled within a range from 0.2 to 4 by controlling the temperature at the vapor outlet.

2. The process of claim 1, wherein step (1B) further comprises supplying methylcyclopentane into the dehydrogenation reactor at a concentration from 100 ppm to 5 wt %, based on the total weight of benzene, cyclohexane, and methylcyclopentane.

3. The process of claim 1, wherein step (1B) comprises supplying at least a portion of the benzene, a portion of the hydrogen and a portion of the cyclohexane in a single stream to the dehydrogenation reactor.

4. The process of claim 3, wherein step (1B) comprises supplying all of the benzene, all of the hydrogen and all of the cyclohexane and optionally all of the methylcyclopentane via the benzene-containing stream provided in step (1A) into the dehydrogenation reactor.

5. The process of claim 4, wherein the benzene-containing stream is supplied from a single vapor outlet of a single condensation separation system.

6. The process of claim 1, wherein in step (1B) the molar ratio of hydrogen to benzene in the dehydrogenation reactor is controlled within a range from 1.0 to 3.0.

7. The process of claim 1, wherein in step (1B) the partial pressure of hydrogen in the dehydrogenation reactor is maintained in a range from 60 kPa to 800 kPa.

8. The process of claim 1, wherein in step (1B) the variation of the total absolute pressure at the vapor outlet of the condensation separation system is controlled within 50 kPa.

9. The process of claim 1, wherein in step (1B) the average of the total absolute pressure at the vapor outlet is in a range from 50 kPa to 300 kPa.

10. The process of claim 1, wherein the dehydrogenation condition comprises a temperature in a range from 350° C. to 550° C.

11. The process of claim 1, wherein the partial pressure of benzene supplied in step (1B) is controlled by controlling the temperature of the vapor phase of the condensation separation system.

12. The process of claim 1, wherein the temperature of the vapor phase is controlled within a range from 40° C. to 170° C.

13. The process of claim 12, wherein the variation of the temperature of the vapor phase is controlled within 20° C.

14. The process of claim 1, wherein step (1A) comprises:

(1A-I) producing a material stream comprising benzene, cyclohexane, and hydrogen;

(1A-II) separating the material stream into the liquid phase and the vapor phase in equilibrium in the condensation separation system; and (1A-III) providing the vapor phase as the benzene-containing stream.

15. The process of claim 14, wherein step (1A-I) comprises:

(1A-I-1) contacting benzene with hydrogen in the presence of a hydroalkylation catalyst under a hydroalkylation condition to produce a hydroalkylation effluent comprising benzene, cyclohexane, hydrogen, and cyclohexylbenzene;

(1A-I-2) separating at least a portion of the hydroalkylation effluent to produce a first fraction comprising cyclohexylbenzene at a concentration higher than the hydroalkylation effluent and a second fraction comprising benzene, cyclohexane, and hydrogen; and (1A-I-3) obtaining the material stream comprising benzene, cyclohexane, and hydrogen from the second fraction.

16. The process of claim 15, wherein in step (1A-I-1), the hydroalkylation effluent further comprises methylcyclopentane, and in step (1A-I-3), the material stream further comprises methylcyclopentane at a concentration in a range from 100 ppm to 5 wt %, based on the total weight of benzene, cyclohexane, and methylcyclopentane therein.

17. A process for making cyclohexylbenzene, the process comprising:

(2A) contacting benzene with hydrogen in the presence of a hydroalkylation catalyst under a hydroalkylation condition to produce a hydroalkylation effluent comprising benzene, cyclohexylbenzene, cyclohexane, and hydrogen;

(2B) separating at least a portion of the hydroalkylation effluent to produce a first fraction comprising cyclohexylbenzene at a higher concentration than the hydroalkylation effluent and a second fraction comprising benzene, cyclohexane, and hydrogen;

(2C) separating at least a portion of the second fraction in a condensation separation system into a liquid phase and a vapor phase in equilibrium with the liquid phase, where the partial pressure of benzene in the vapor phase is controlled;

(2D) supplying the vapor phase from a vapor outlet in the condensation separation system into a dehydrogenation reactor; and (2E) contacting at least a portion of the cyclohexane in the vapor phase with a dehydrogenation catalyst in the dehydrogenation reactor under a dehydrogenation condition to produce a dehydrogenation effluent comprising benzene and hydrogen;

wherein the molar ratio of hydrogen to benzene in the dehydrogenation reactor is controlled within a range from 0.2 to 4 by controlling the temperature at the vapor outlet.

18. The process of claim 17, wherein in step (2A), the hydroalkylation effluent further comprises methylcyclopentane, and in step (2D), the vapor phase comprises methylcyclopentane at a concentration in a range from 100 ppm to 5 wt %, based on the total weight of benzene, cyclohexane, and methylcyclopentane in the reaction medium.

19. The process of claim 17, the process further comprising:
(2F) recycling at least a portion of the benzene and/or the hydrogen contained in the dehydrogenation effluent from step (2E) to the contacting step (2A).

20. The process of claim 17, wherein in step (2C), the partial pressure of hydrogen is controlled within a range from 5 kPa to 300 kPa.

21. The process of claim 17, wherein in step (2C), the partial pressure of benzene is controlled by controlling the temperature of the vapor phase within a range from 40° C. to 170° C.

22. The process of claim 21, wherein in step (2C), the variation of the temperature of the vapor phase is controlled within 20° C.

23. The process of claim 17, wherein in step (2E), the dehydrogenation condition comprises at least one of:
(a) a temperature of the reaction medium in the dehydrogenation reactor in a range from 350° C. to 550° C.; and
(b) an absolute pressure in the dehydrogenation reactor in a range from 60 kPa to 800 kPa.

24. The process of claim 17, wherein in step (2E), the dehydrogenation catalyst comprises a group 8-10 metal supported on an oxide substrate.

25. A process for making phenol and/or cyclohexanone, the process comprising:
(3A) producing cyclohexylbenzene in a process according to claim 17;
(3B) oxidizing at least a portion of the cyclohexylbenzene to obtain cyclohexylbenzene hydroperoxide; and
(3C) subjecting at least a portion of the cyclohexylbenzene hydroperoxide to a cleavage reaction to obtain a cleavage reaction effluent comprising phenol and cyclohexanone.

* * * * *